United States Patent
Apte (12)

(10) Patent No.: US 6,713,064 B1
(45) Date of Patent: *Mar. 30, 2004

(54) IMMUNE ENHANCING AGENT FOR TREATING HIV INFECTED HUMANS

(76) Inventor: Sateesh N. Apte, 2817 Crow Canyon Rd., San Ramon, CA (US) 94583-1639

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/879,099

(22) Filed: Jun. 19, 1997

Related U.S. Application Data

(63) Continuation of application No. 08/364,600, filed on Dec. 27, 1994, now abandoned.

(51) Int. Cl.$^7$ ................................................. A61K 39/21
(52) U.S. Cl. .................................. 424/188.1; 424/188.1
(58) Field of Search .......................... 424/188.1, 208.1, 424/198.1, 204.1, 205.1, 93.1, 93.2; 435/236, 91.33, 91.42, 172.3, 320.1, 440, 235.1

(56) References Cited

U.S. PATENT DOCUMENTS 5,851,813 A * 12/1998 Desrosiers ............... 435/235.1

* cited by examiner

*Primary Examiner*—James Housel
*Assistant Examiner*—Jeffrey S. Parkin

(57) ABSTRACT

Human immunodeficiency virus (HIV) is the primary etiologic agent for the acquired immune deficiency syndrome (AIDS). HIV exhibits considerable genotypic and phenotypic variability as manifested by different replicative kinetics, susceptibility to serum neutralization, antiviral drug resistance, cytopathic effects, and host-cell range specificity. Infection by HIV leads to progressive deterioration of cell-mediated immune responses making infected patients susceptible to a variety of opportunistic infections, such as *pneumocystis carinii* pneumonia (PCP), as well as, to the development of tumors such as Kaposi's sarcoma (KS). While the use of live-attenuated viruses to treat HIV infection has been proposed, to date researchers have been unable to demonstrate their efficacy in a clinical setting. The claimed invention addresses this defect by providing therapeutic compositions and methods of treatment employing viral suspensions prepared from cells transfected with a recombinant HIV-1 nef-deficient molecular clone. The HIV-1 nef gene product is required for efficient viral replication and pathogenicity in vivo. Nef may exert its effects through the downregulation of CD4 by endocytosis and lysosomal degradation, although other activities have also been ascribed to this gene product. Accordingly, this gene product was targeted for inactivation and a recombinant HIV-1$_{ELI}$ molecular clone was generated containing an NcoI/XhoI nef deletion. Suspensions comprising viral particles generated from cells transfected with the recombinant clone were prepared and administered to HIV-infected patients. Patients receiving these suspensions displayed a statistically significant reduction in viral burden and increase in CD4$^+$ lymphocyte counts during the study. The claimed compositions should facilitate the reduction of viral burden and the restoration of CD4$^+$ lymphocyte levels in HIV-1-infected subjects.

3 Claims, No Drawings

IMMUNE ENHANCING AGENT FOR TREATING HIV INFECTED HUMANS

This is a continuation, of application Ser. No 08/364,600, filed Dec. 27, 1994 now abandoned.

BACKGROUND OF THE INVENTION

1. Field of the Invention

This invention relates to treatment and prevention of Human Immunodeficiency Virus (HIV) by using a live genetically altered HIV virus vaccine.

2. Description of the Prior Art

To the best of this inventor's knowledge, no prior art employing a similar invention for treatment or prevention exists.

Human Immunodeficiency Virus (HIV) is th e primary etiologic agent for the acquired immunodeficiency syndrome (AIDS). HIV exhibits high genetic variation, which results in a wide variety of biological phenotypes displayed by various strains of the virus and also by the same strain of the virus in a single patient at different times. Phenotypic heterogeneity is found in replication kinetics, susceptibility to serum neutralization, anti-viral drug resistance, induction of cytopathicity and host-cell range specificity. The two main sub-types HIV-1 and HIV-2 are members of a group of closely related human and non-human primate lentiviruses which are RNA retroviruses.

Infection by the HIV leads to progressive deterioration of cell mediated immune system making the victim susceptible to a variety of opportunistic infections such as *pneumocystis carinii* pneumonia (PCP) and tumors such as Kaposi's sarcoma (KS). It is known that the mechanism of the destruction of the immune system is the cytopathic effect of HIV on $CD4^+$ $T_{HELPER}$ lymphocytes which are instrumental in proper functioning of cell mediated immunity.

AIDS and HIV infection initially involved homosexual men, intravenous drug users and hemophiliacs in the United States and Europe. However, heterosexual infection has become common and rampant in Africa (particularly in Rwanda, Burundi, Zaire and Kenya), Brazil, India, Myanmar and Thailand. According to the World Health Organization, in excess of 10,000,000 people world-wide are estimated to be infected with the HIV. The available data indicates that almost all of these infected individuals would die for lack of an effective treatment.

Humoral antibody response mediated by B Lymphocytes is usually strong in infected individuals with high antibody titres in those infected to the envelope proteins gp120, gp41 and gag proteins p24, p17 and p15. Unfortunately, this does not provide any protection from continued and relentless infection and progression of the disease mainly due to cell-to-cell transmission of infection and inhibition of cytotoxic T lymphocytes perhaps by inhibition of the IL-2 (interleukin 2) signalling. The US National Institutes of Health recently abandoned phase III and phase IV trials of vaccines derived from various viral proteins of HIV because of disappointing results in earlier phases. Similarly, cellular response against HIV is initially strong with an increase in cytotoxic ("killer") T lymphocytes (CTL). Unfortunately, this breaks down soon after infection due to genetic variations in the gag CTL epitopes which allows the virus to escape CTL recognition. (Phillips R E et al; Nature 345:453, 1991)

Various drugs have also been approved for treatment of HIV infection such as zidovudine which interfere with the virus's nucleotide sequencing. While these were felt to be very promising in the earlier stages, development of resistance to them has caused a considerable amount of disappointment and frustration.

A variety of other approaches have been postulated. Professor Jonas Salk, in his commentary in Nature noted that as the disease progresses, titres of antibodies to gp41 and virus neutralizing antibody remain constant but the level of anti-p24 antibody which correlates with the presence of antibody dependent cell cytotoxicity (ADCC) and antibody to reverse transcriptase decline. He proposed treatment of symptomatic HIV infected patients with sera from asymptomatic HIV infected patients. He further hypothesized that HIV immunogens given to HIV infected patients would be protective. (Salk J; Prospects for the control of AIDS by immunizing seropositive individuals. Nature 327:473–476, 1987)

Live-attenuated viruses and dead virions have been hypothesized but no researcher has yet tried these either for prevention or treatment of HIV infection in humans in a meaningful manner.

SIV (Simian Immunodeficiency Virus) is a primate lentivirus with various strains that affect African green monkeys, macaque monkeys, sooty-mangabee monkeys, rhesus monkeys and chimpanzees. SIV infection in monkeys is widely used to study the physiology and pathology of the primate lentiviruses. A great deal of research has been done by attempting to infect monkeys with artificially created mutants of the SIV to determine their relative infectivity. Many of these studies focused on the role of the nef gene in the physiology of virus life cycle. The nef gene is present in all primate lentiviruses sequenced to-date. The gene consists of an open reading frame beginning within or immediately after the 3' end of the env gene and overlaps the U3 portion of the 3' long terminal repeat. The gene was previously named F, 3'-orf or B-orf. It is expressed in vivo as determined by antibodies to the nef gene product in infected individuals. Luria et al have shown that at least some nef gene products block the induction of IL-2 (interleukin 2) mRNA in lymphoid cells triggered by activating agents PMA, PHA and/or antibodies against CD3, TCR or CD2 (Luria S, Chambers I, Berg P; Proc Natl Acad Sci USA 88:5326, 1991). Kestler et al have found rapid reversion of of stop codon point mutations in nef to open forms in vivo, demonstrating selective pressure for open, presumably functional forms of nef. (Kestler H W et al; Cell, 65:651, 1991) It was further shown that nef is necessary for vigorous virus replication in rhesus monkeys, for maintaining normal virus loads and for induction of the disease. Animals inoculated with nef-deletion mutants have remained disease free for at least 3 years while wild-type virus infected animals all developed AIDS and died. It has also been demonstrated that nef deletion increases viral replication but it is postulated that the responses to nef deletion are different in vivo and in vitro. (Gibbs J S and Desrosiers R C in Human Retroviruses, Cullen B R, ed, Oxford University Press, NY, 1993)

It became the first object of this invention, therefore, to produce an HIV virus clone by utilizing recombinant technology in which a substantial portion of the nef gene is deleted while preserving the remaining open reading frames, particularly tat, pol, gag, env and vpr. It is a further object of this invention to inject patients infected with HIV with this nef deleted recombinant virus and provide a cure by means of one or more of a) by allowing normal IL2 and IFNγ production in $T_{HELPER}$ cells thus activating B lymphocytes and cytotoxic ("killer") T lymphocytes (CTL) to recognize HIV antigen displaying cells, b) by continually activating, stimulating and maintaining a cell mediated immune response to wild-type HIV via cytotoxic T Lymphocytes (CTL), c) and by competing with the wild-type HIV for potential hosts and thus increasing the likelihood of exposure of the wild-type HIV to humoral antibodies to gp120, gp41 and gag proteins.

The second object of this invention is to provide prophylactic immunization in high risk individuals such as commercial sex workers by treatment with the nef deleted mutant virus which is a subject of this invention by providing a line of cytotoxic T lymphocytes with specificity to cells expressing any of the HIV proteins and which would create a semi-permanent memory stems of CTLs lasting a long time. Infection by wild-type HIV would, in these individuals be handled quickly, efficiently and effectively.

SUMMARY OF THE INVENTION

A recombinant clone of HIV-$1_{ELI}$ isolate with its nef open reading frame deleted was constructed from a plasmid vector by endonuclease cleaving at Nco I and Xho I sites and filling in the open ends with an oligonucleotide. The resultant plasmid DNA was screened and transfected by using DEAE dextran into HuT 78 cell line. HIV virus propagation was confirmed by monitoring proteins gp41, p24, p17 and p15, by monitoring reverse transcriptase activity and by electron micoscopic identification of virions. Virus particles were separated from supernatant medium and frozen in liquid nitrogen until use. For treatment of HIV infection, after baseline diagnostic procedures including confirmation of HIV infection and CD4–CD8 cell counts, a skin test for allegic reaction and an informed consent, approximately 200,000,000 virus particles will be injected intravenously. This will be followed by semimonthly monitoring of CD4 counts and a booster dose of another 200,000,000 virus particles intravenously. This will be followed by monthly monitoring of CD4 counts for one year. According to the invention, patients are expected to have a normal CD4 count in 6–9 months and will have restored immune systems in 1 year. For prevention of wild-type HIV infection in high risk populations, approximately 1,000,000 virus particles will be injected subcutaneously, the subjects observed for sufficient time to ensure absence of untoward effects such as an anaphylactic reaction. Immunity in this population will be ascertained by seroconversion and wild-type HIV infection can be diagnosed by utilizing enzyme linked immunosorbent assays for detection of antibodies to the nef gene product.

DESCRIPTION OF THE PREFERRED EMBODIMENT

HuT 78 Cells, a human lymphoid cell line was obtained from the American Type Culture Collection (Rockville, Md.) and propagated in Dulbecco's modified Eagle's medium (Gibco, Grand Island, N.Y.) containing 10% heated (56° F., 30 minutes) calf serum (Sigma Chemical Company, St. Louis, Mo.) and 10% interleukin 2—a T cell growth factor (Meloy laboratories, Springfield, Va.). Cells were grown on plastic tissue clulture dishes (Falcon) and transferred using trypsin with EDTA (Gibco, Grand Island, N.Y.). This cell line was inoculated with peripheral blood mononuclear cells (PBMCs) from an AIDS patient infected with the HIV-$1_{ELI}$ strain. The PBMCs were first prepared by banding over Ficoll-diatrizoate (density, 1.077 to 1.080 g/ml at 20° C.)(Pharmacia LKB Biotechnology, Uppsala, Sweden). The PBMCs were washed with RPMI 1640 medium, stimulated for 5 days with 1 µg/ml of phytohemagglutinin (Sigma Chemical Co., St. Louis, Mo.) and washed free of phytohemagglutinin prior to inoculation. The molecular cloning techniques were used as described by Maniatis T, Fritsch, EF et al (Molecular Cloning, a Laboratory Manual, Cold Spring Harbor Laboratory, Cold Spring Harbor, N.Y.). By using a non-cutter restriction endonuclease of HIV-$1_{ELI}$ (New England Biolabs, Beverly, Mass.) from total cell DNA of the infected cell line, integrated proviral DNA with flanking cellular sequences were cloned into the Xba I site of bacteriophage J1 (Promega Biotec, Madison, Wis.) giving rise to a recombinant phage clone λHXELI. A vector SP65gpt was constructed by ligating Bam HI-Pvu II fragment of plasmid pSV2gpt into the Bam HI-Pvu II sites of SP65 (Promega Biotec, Madison, Wis.). A 12.5 Kilobase (kb) Hpa I-Xba I fragment of the clone λHXELI was blunt-ended with Klenow fragment of DNA polymerase I and cloned into similarly blunt-ended Bam HI to Eco RI sites of vector SP65gpt. The resultant clone HXELIgpt had the HIV-$1_{ELI}$ and xanthine guanine phosphoribosyl transferase (gpt) sequences in identical transcriptional orientation. The provirus containing plasmid vector was digested with Nco I (Boehringer Mannheim Biochemicals, Mannheim, Germany) and Xho I (New England Biolabs, Beverly, Mass.) restriction endonucleases followed by a filling in the ends with an oligonucleotide constructed on a Biosearch Cyclone synthesizer, reverse transcriptase and dNTPs, followed by ligation of the blunt ends. Plasmids were screened by electrophoresis on 0.8% agarose gels (Sigma Chemicals, St. Louis, Mo.) for derivatives of HXELIgpt containing nef deletion. The exact coordinates of the deletion were confirmed by DNA sequencing with chain terminating inhibitors of DNA polymerase -2', 3'-dideoxy and arabinonucleoside analogues of the normal deoxynucleoside triphosphate (ddCTP was obtained from Collaborative Research, Inc., Waltham, Mass., araATP and araCTP were obtained from P-L Biochemicals, Inc., Milwaukee, Wis.) as described by Sanger, F, Nicklsen, S et al (Proc Natl Acad of Sci 74:5463–5467, 1977). Heteroduplex DNA was subjected to ethanol precipitation and and resuspended in sterile water. Serial dilutions of DNA were prepared to a final volume of 80 micL. To each sample of DNA was added 20 µL DEAE dextran (molecular weight $5\times10^5$) obtained from Pharmacia in a concentration of 2 mg/ml after sterilizing by autoclaving and 100 µL of twofold concentrated serum-free Dulbecco's modified Eagle's medium (Gibco, Grand Island, N.Y.). The HuT 78 cells described above were transferred to fresh plates 24 hours prior to transfection to ascertain an exponential growth. These growing cells were removed from plates with 0.1% trypsin with EDTA (Gibco, Grand Island, N.Y.) in Tris-buffered isotonic saline at pH 7.2 (Sigma Chemicals, St. Louis, Mo.), mixed with fresh Dulbecco's modified Eagle's medium containing heated calf serum as described above to inactivate the trypsin and counted with a Coulter counter. $6\times10^5$ cells were added to 2 ml Dulbecco's modified Eagle's medium containing serum in 12 mm×75 mm clear plastic tubes (Falcon #2058). The tubes were centrifuged at 5000 rpm for 1 minute. The medium was withdrawn carefully using a pipette with an aspirator. A 100 µL sample of the DNA dilution was added to each tube. The tubes were gently shaken and transferred to a 37° C. $CO_2$ incubator for 1 hr. The rack was gently shaken every 15 minutes. At the end of the incubation, 2 ml of fresh Dulbecco's modified Eagle's medium containing heated calf serum as described above was added to each tube, the tubes were shaken, centrifuged and the medium aspirated as described above. The cells were then resuspended in 2 ml of fresh Dulbecco's modified Eagle's medium containing heated calf serum as described above and incubated at 37° C. in a 5% $CO_2$ incubator. The cultures were monitored for appearance of HIV-1 gag and env products p17, p24 and gp41, reverse transcriptase activity and virions as seen by electron microscopy as is readily known to those knowledgeable in the art. Virus containing supernatant of the cultures was filtered through a millipore filter (filter size 0.45 µm, Millipore Corp., Bedford, Mass.) and placed in sterile vials so as to contain about 200,000,000 virion particles per ml. The sterile vials were stored in liquid nitrogen.

EXAMPLE 1

Two volunteers (S1 and S2), both commercial sex workers in India became HIV positive in 1989. Since then, both have had a downhill course with diarrhoea, weight loss, candida and CMV infections. Their CD4 counts were 327 and 258 respectively. Families and friends of both had deserted them due to their HIV infection and they had almost no support structure left. After a detailed informed consent and a thorough discussion of all the risks involved with the use of the present invention, these individuals were given a physical, confirmatory Western Blot tests to ensure HIV status, baseline CD4–CD8 cell counts and a skin test for sensitivity to the viral suspension, both were given 1 ml of recombinant viral suspension containing approximately 200,000,000 virus particles intravenously. The patients were quarantined in an isolated facility and all personnel coming in contact with them used communicable disease precautions. The patients' CD4 counts were recorded one month after the first injection and they were given a second injection of equal dose intravenously. Their CD4 counts were recorded once again, 4–6 weeks after the booster. The patients started gaining weight in approximately 4–6 weeks after the first injection and their CD4 counts increased as shown in the accompanying table. They became asymptomatic in 3 and 4.5 months respectively.

|  | Prior to Vaccine | After Vaccine & Booster |
| --- | --- | --- |
| Patient S1 | 240/mm$^3$ | 1051/mm$^3$ |
| Patient S2 | 385/mm$^3$ | 1233/mm$^3$ |

100 SCID (Severe Combined Immunodeficiency Syndrome) mice with human immune system transplanted were separated into control and experimental group of 50 mice each. The experimental group was infected with an intravenous injection of 1 million virions of the nef deleted virus subject of the preferred embodiment. 1 month after this injection, both the groups were infected with wild-type HIV-1 virions and infected lymphocytes. 1 month after the infection, 10 mice from each group were sacrificed and their lymphoid tissues examined. The pathologic examination revealed a severe loss of follicular dendritic cells, considerable syncytium formations and the peripheral blood with an average reduction of 38.6% in CD4 cell counts in the control group. The experimental group revealed minimal pathologic changes and no significant reduction in the CD4 cell counts. After 2 more months had elapsed, 58% of the animals in the control group were dead as a result of immunodeficiency caused by the wild-type HIV-1 infection whereas no animals in the experimental group died as a result of immunodeficiency. This observation is statistically significant ($p<0.001$). 20 animals from the experimental group were again infected with wild-type HIV-1 as described above and again, there was no pathologic response.

Since the recombinant virus which is a subject of this invention has been found to be non-pathogenic and affording immunity from the CD4 cytotoxic effects of wild-type HIV as described above, the following protocol is established for prophylaxis against wild type HIV infection in high risk individuals:

1. A thorough physical examination and education regarding HIV infection.
2. A detailed discussion of the risks of prophylaxis with recombinant nef deleted HIV virus and procurement of an informed consent. The discussion will include the inability to diagnose wild-type HIV infections from standard tests and the need to perform a special ELISA (enzyme linked immunosorbent assay) to detect antibodies to the nef protein.
3. Approximately 1,000,000 virus particles suspended in 0.5 ml to be given subcutaneously.
4. Subjects will be observed for a sufficient time to ensure lack of untoward reactions such as an anaphylactic reaction.
5. Seroconversion will be monitored for successful immune response to the recombinant virus.

It is understood that the foregoing description and examples have been given merely by way of illustration and that modifications and variations may be made therein without departing from the spirit and scope of the present invention.

CONCLUSION, RAMIFICATIONS & SCOPE

Even though just one potential use of a recombinant retrovirus has been described, the principle of the invention has many far reaching implications. The principle could be used broadly for prevention and treatment of other retroviral infections such as the leukemia caused by HTLV viruses. There may be other pathogenic retroviruses that have yet to be discovered in whom this principle could be used. It is certainly probable that this invention could be modified to alter the location and extent of the gene deletion and/or expand the sites of deletions. It is also feasible to create a similar gene deletion by using alternative methods to those described in the preferred embodiment of the invention above.

What is claimed is:

1. A method for increasing or restoring CD4$^+$ lymphocyte levels in human immunodeficiency virus type 1 (HIV-1)-infected subjects comprising the following steps:
    a) preparing a therapeutic suspension comprising isolated and purified replication-impaired HIV-1 nef-deficient viral particles prepared from cells transfected with a recombinant replication-impaired HIV-1 molecular clone having a nef-deletion, wherein said viral particles are suspended in a pharmaceutically acceptable medium; and
    b) administering said suspension to an HIV-1-infected subject; wherein said administration results in a statistically significant increase in CD4$^+$ lymphocyte cell count in said patient and improved clinical outcome.

2. The method of claim 1 wherein said particles are prepared from cells transfected with a recombinant replication-impaired HIV-1$_{ELI}$ molecular clone having a nef-deletion.

3. The method of claim 2 wherein said recombinant replication-impaired HIV-1$_{ELI}$ molecular clone has a nef-deletion between the endonuclease cleavage sites Nco I and Xho I.

* * * * *